United States Patent
Osadchy et al.

(10) Patent No.: US 8,478,379 B2
(45) Date of Patent: Jul. 2, 2013

(54) PROBE VISUALIZATION BASED ON MECHANICAL PROPERTIES

(75) Inventors: Daniel Osadchy, Haifa (IL); Meir Bar-Tal, Zichron Ya'acov (IL)

(73) Assignee: Biosense Webster, Inc., Diamond Bar, CA (US)

( * ) Notice: Subject to any disclaimer, the term of this patent is extended or adjusted under 35 U.S.C. 154(b) by 927 days.

(21) Appl. No.: 12/574,967

(22) Filed: Oct. 7, 2009

(65) Prior Publication Data

US 2010/0121174 A1  May 13, 2010

Related U.S. Application Data (60) Provisional application No. 61/113,712, filed on Nov. 12, 2008.

(51) Int. Cl.
 *A61B 5/05* (2006.01)
(52) U.S. Cl.
 USPC ............ 600/407; 600/424; 600/427; 600/447
(58) Field of Classification Search
 USPC .................................. 600/407, 424, 427, 447
 See application file for complete search history.

(56) References Cited

U.S. PATENT DOCUMENTS

| 5,983,126 | A | 11/1999 | Wittkampf | |
|---|---|---|---|---|
| 6,129,668 | A * | 10/2000 | Haynor et al. | 600/424 |
| 7,706,860 | B2 * | 4/2010 | McGee | 600/424 |
| 8,303,505 | B2 * | 11/2012 | Webler et al. | 600/447 |
| 2006/0173251 | A1 | 8/2006 | Govari et al. | |
| 2007/0038078 | A1 | 2/2007 | Osadchy | |
| 2008/0009711 | A1 | 1/2008 | Govari et al. | |
| 2008/0043902 | A1 | 2/2008 | Viswanathan | |

FOREIGN PATENT DOCUMENTS

EP 1 797 812 B1 6/2007

OTHER PUBLICATIONS

EP Search Report EP 09 25 2595 Dated Jan. 26, 2010.

* cited by examiner

*Primary Examiner* — Unsu Jung
*Assistant Examiner* — Joel Lamprecht
(74) *Attorney, Agent, or Firm* — Louis J. Capezzuto (57) ABSTRACT

A method for visualization includes receiving an input indicative of respective apparent coordinates of a plurality of points disposed along a length of a probe inside a body of a subject, and applying a model of known mechanical properties of the probe to the apparent coordinates so as to compute a cost function with respect to shapes that can be assumed by the probe in the body. A shape is chosen responsively to the cost function, and corrected coordinates of the points along the length of the probe are generated based on the shape. The representation of the probe using the corrected coordinates is then displayed.

22 Claims, 4 Drawing Sheets

PROBE VISUALIZATION BASED ON MECHANICAL PROPERTIES

RELATED APPLICATION

This application claims the benefit of U.S. Provisional Patent Application 61/113,712, filed Nov. 12, 2008, which is incorporated herein by reference.

FIELD OF THE INVENTION

The present invention relates generally to sensing the position of an object placed within a living body, and specifically to detection and compensation for artifacts experienced during position sensing of a probe in a living body.

BACKGROUND

A wide range of medical procedures involve placing objects, such as sensors, tubes, catheters, dispensing devices, and implants, within the body. Position sensing systems have been developed for tracking such objects. For example, U.S. Pat. No. 5,983,126, to Wittkampf, whose disclosure is incorporated herein by reference, describes a system in which catheter position is detected using electrical impedance methods. U.S. Patent Application Publications 2006/0173251, to Govari et al., and 2007/0038078, to Osadchy, describe methods for sensing the position of a probe by passing electrical currents through the body between an electrode on the probe and a plurality of locations on a surface of the body. These methods likewise use the electrical impedance of the body in sensing probe position.

When using impedance-based measurement technology for determining the position of a probe (e.g., a catheter), it has been found that if the probe image is not constrained to assume realistic shapes and positions, sudden fluctuations can occur, which are disconcerting to the physician who is viewing the patient monitor. U.S. Patent Application Publication 2008/0009711, whose disclosure is incorporated herein by reference, describes methods for enhanced visualization of a probe when such measurement technologies are used by stabilizing a displayed image of the probe.

SUMMARY OF THE INVENTION

There is thus provided, in accordance with an embodiment of the invention, a method for visualization, including receiving an input indicative of respective apparent coordinates of a plurality of points disposed along a length of a probe inside a body of a subject, applying a model of known mechanical properties of the probe to the apparent coordinates so as to compute a cost function with respect to shapes that can be assumed by the probe in the body, choosing a shape responsively to the cost function, generating corrected coordinates of the points along the length of the probe based on the shape, and displaying a representation of the probe using the corrected coordinates.

There is also provided in accordance with an embodiment of the invention, a computer program product for controlling a peripheral device, the computer program product including a computer usable medium having computer usable code embodied therewith, the computer usable program code including computer usable code configured for receiving an input indicative of respective apparent coordinates of a plurality of points disposed along a length of a probe inside a body of a subject, computer usable code configured for applying a model of known mechanical properties of the probe to the apparent coordinates so as to compute a cost function with respect to shapes that can be assumed by the probe in the body, computer usable code configured for choosing a shape responsively to the cost function, computer usable code configured for generating corrected coordinates of the points along the length of the probe based on the shape, and computer usable code configured for displaying a representation of the probe using the corrected coordinates.

There is further provided in accordance with an embodiment of the invention, a probe visualization apparatus, including an interface, which is configured to receive an input indicative of respective apparent coordinates of a plurality of points disposed along a length of a probe inside a body of a subject, and a processor, which is configured to receive the input from the interface, apply a model of known mechanical properties of the probe to the apparent coordinates so as to compute a cost function with respect to shapes that can be assumed by the probe in the body, choose a shape responsively to the cost function, and generate corrected coordinates of the plurality of position transducers along the length of the probe based on the shape.

BRIEF DESCRIPTION OF THE DRAWINGS

The invention is herein described, by way of example only, with reference to the accompanying drawings, wherein.

DETAILED DESCRIPTION OF EMBODIMENTS

The following notation is used throughout this document:

| Term | Definition |
| --- | --- |
| ACL | Accurate Current Location |
| BFGS | Broyden-Fletcher-Goldfarb-Shanno |
| CPU | Central Processing Unit |
| I/O | Input/Output |
| SAS | Single-Axis magnetic Sensors |
| TAS | Three-Axis magnetic Sensors |

Some embodiments of the present invention enable a medical professional to more accurately visualize a flexible probe in a body of a subject by applying a model of the mechanical properties of the probe to apparent coordinates received from points on the probe. A processor first applies the model of known mechanical properties of the probe to the apparent coordinates, in order to compute a cost function with respect to shapes that can be assumed by the probe in the body. The processor then chooses a shape for the probe, responsively to the cost function, and then generates a set of corrected coordinates of the points along the length of the probe based on the shape. Using the corrected coordinates, a more accurate representation of the probe can be displayed.

Figure 1:
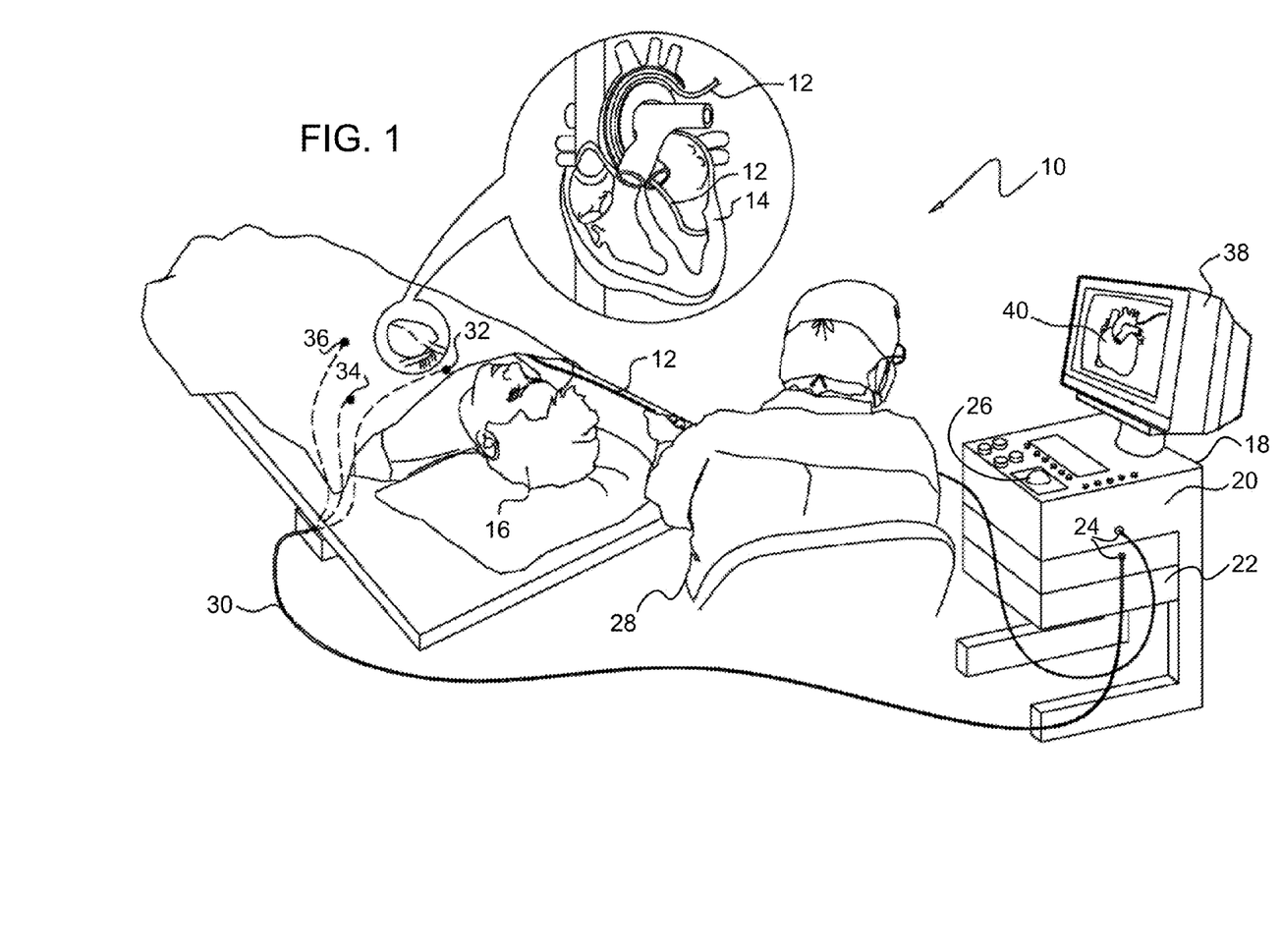
FIG. 1 is a schematic pictorial illustration of a position sensing system, in accordance with an embodiment of the present invention.
Figure 2A:
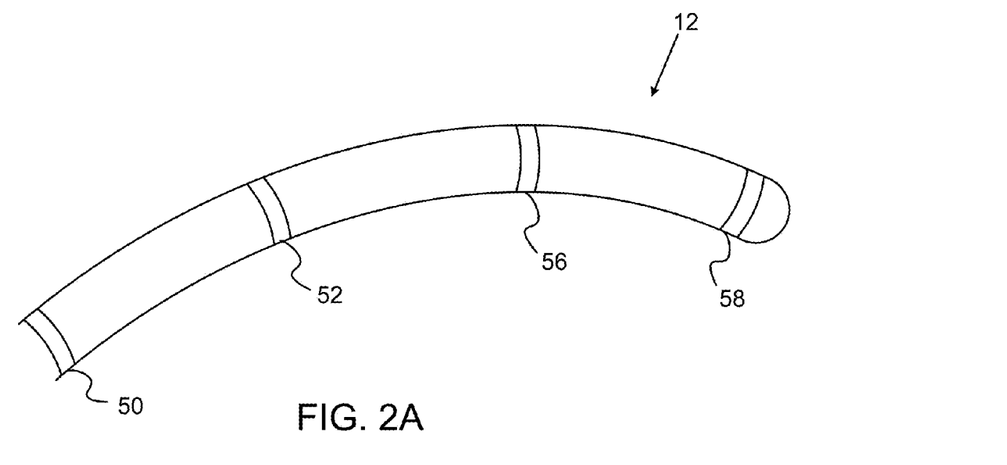
FIG. 2A is a schematic side view of a probe deviating from its free shape, in accordance with an embodiment of the present invention.

FIG. 1 is an illustration of a position sensing system 10, which is constructed and operative in accordance with a disclosed embodiment of the invention. System 10 is used in determining the position of a flexible probe 12, such as a catheter, which is inserted into an internal body cavity, such as a chamber of a heart 14 in a subject 16. Typically, probe 12 is used for diagnostic or therapeutic treatment, such as mapping electrical potentials in heart 14 or performing ablation of heart tissue. Probe 12 or other intrabody devices may alternatively be used for other purposes, by itself or in conjunction with other treatment devices. The distal tip of probe 12 comprises one or more electrodes (FIG. 2A). These electrodes are connected by wires (not shown) through the insertion tube of probe 12 to driver circuitry in a control unit 18, as described hereinbelow.

Control unit 18 is connected by wires through a cable 30 to body surface electrodes, which typically comprise adhesive skin patches 32, 34, 36. In alternative embodiments of the invention, the electrodes on the body surface may vary in number and may take other forms, such as subcutaneous probes or a handheld device operated by a medical professional 28. Patches 32, 34, 36 may be placed at any convenient locations on the body surface in the vicinity of probe 12. For example, for cardiac applications, patches 32, 34, 36 are typically placed around the chest of subject 16. There is no special requirement regarding the orientation of patches relative to each other or to the coordinates of the body, although greater accuracy may be achieved if the patches are spaced apart, rather than clustered in one location. There is no requirement that the placement of the patches be along fixed axes. Consequently, patch placement can be determined in order to interfere as little as possible with the medical procedure being performed.

Control unit 18 determines position coordinates of probe 12 inside heart 14 based on the impedance measured between probe 12 and patches 32, 34, 36. Control unit 18 drives a display 38, which shows the position of probe 12 inside subject 16. Probe 12 may be used in generating a map 40 of the heart. The position of probe 12 may be superimposed on map 40 or on another image of the heart.

Control unit 18 is a computer system comprising a processor, such as a central processing unit (CPU) 20, which is programmed in software to carry out the functions that are described hereinbelow. Control unit 18 also includes a magnetic or semiconductor-based storage device 22 for storing application programs and data. A data I/O communications interface 24 enables control unit 18 to interact with probe 12 and patches 32, 34, 36. Medical professional 28 controls the operation of control unit 18 via a group of input devices 26.

Although FIG. 1 shows a particular system configuration, other system configurations can also be employed to implement embodiments of the present invention, and are thus considered to be within the spirit and scope of this invention. For example, the methods described hereinbelow may be applied in correcting position measurements made using position transducers of other types, such as magnetic or ultrasonic position sensors. The term "position transducer" as used herein refers to an element mounted on the probe which causes control unit 18 to receive signals indicative of the coordinates of the element. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in visualizing the locations not only of catheters, but also of probes of other types, both in the heart and in other body organs and regions.

The flowcharts and block diagrams in the Figures illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or by combinations of special purpose hardware and computer instructions.

Figure 2B:
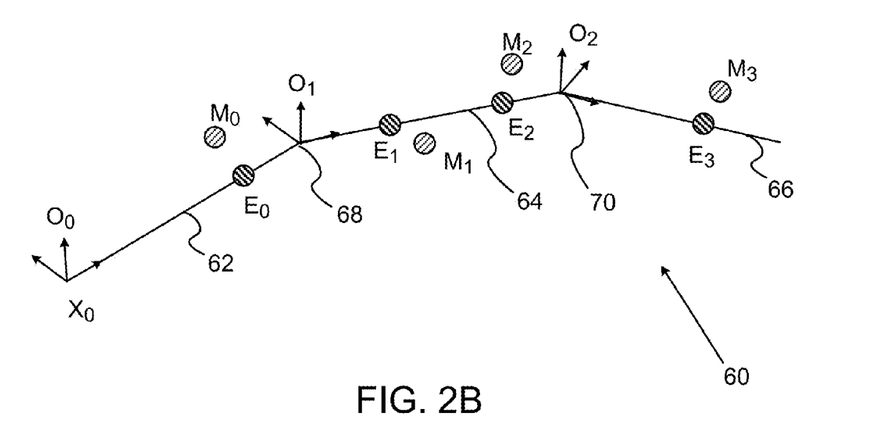
FIG. 2B is a diagram that schematically shows the model geometry of a probe deviating from its free shape, in accordance with an embodiment of the present invention.

FIGS. 2A and 2B are diagrams that schematically show probe 12 deviating from its free shape, in accordance with an embodiment of the present invention. FIG. 2A shows a representation of the actual curvature of probe 12 in heart 14, wherein probe 12 comprises electrodes 50, 52, 56, 58, which serve as position transducers in this embodiment. FIG. 2B is a diagram of a calculated geometrical model 60 of probe 12. The measured locations of electrodes 50, 52, 56, 58, based on the signals received by control unit 18, are respectively represented by points $m_0$, $m_1$, $m_2$ and $m_3$. Alternatively or additionally, in a magnetic position sensing system, the position transducers may comprise single-axis magnetic sensors (SAS), which give position and direction, and/or three-axis magnetic sensors (TAS), which provide position and a complete orientation matrix.

In model 60, points $e_0$, $e_1$, $e_2$ and $e_3$ represent calculated locations of electrodes 50, 52, 56, 58, based on the measured locations of points $m_0$, $m_1$, $m_2$ and $m_3$. A cost function in accordance with an embodiment of the present invention is used to find the best match between the point $e_j$ and $m_j$. Model 60 comprises straight rigid sections 62, 64 and 66, connected by joints 68 and 70 that allow rotation (bending and twisting). The position of section 62 is described by position vector $x_0$, and the orientation of section 62 is given by a matrix $o_0$. Orientation matrix $o_0$ is a local reference frame of section 62 with its $\hat{x}$ and $\hat{y}$ axes being perpendicular to section 62, and the $\hat{z}$ axis pointing along section 62. Section 64 starts at the end of section 62 (i.e., via connecting joint 68), and its orientation is given by matrix $o_1$. Section 66 starts at the end of section 64 (i.e., via connecting joint 70), and its orientation is given by matrix $o_2$. Matrices $o_0$, $o_1$ and $o_2$ describe the actual state (i.e., shape) of the probe, wherein external forces cause the probe to deviate from its free state (i.e., in which no external forces are applied to the probe). Although model geometry 60 comprises three sections, alternative model geometries may comprise either fewer than three or more than three sections.

Embodiments of the present invention determine the best match between the points $e_j$ and the measurements $m_j$ within the constraints of a probe model. Note that the calculated locations of points $e_0$, $e_1$, $e_2$ and $e_3$ are constrained by the model to be on the sections 62, 64 and 66, but the actual position transducers (i.e., electrodes 50, 52, 56 and 58) may not be precisely at these points. The physical properties of probe 12 in its free state are defined by the parameters $\{N, L_k, G_k(d), P_k\}$ wherein:

N—Number of sections.

$L_k$—Section lengths (need not be equal), $0 \leq k < N$.

$G_k(d)$—Rotation matrix as a function of the deflection parameters d for deflectable probes (or a constant matrix for pre-shaped probes), $1 \leq k < N$. This matrix represents the relative rotation between section k and section (k−1) when no external forces are applied (i.e., probe free shape).

$P_k$—List of position transducers on section k, where $0 \leq k < N$. Each position transducer is represented by its distance from the section start, its type (for example, ACL electrode, SAS or TAS magnetic sensor), and its relative importance (its weight in calculating a cost function, denoted by $w_j^{model}$, discussed infra). The list for each section can contain any number of position transducers, including zero.

The physical properties of probe 12 are described by the parameters $\{A_k, B_k\}$ which represent the resistance of a joint between section k and section (k−1) against bending and twisting, respectively.

Frequently, as shown in FIG. 2B, the actual position of probe 12 (as defined by the locations of electrodes 50, 52, 54, 56) differs from points $m_0, m_1, m_2$ and $m_3$. In embodiments of the present invention, a probe model is defined, describing the physical characteristics of probe 12, and CPU 20 applies a probe mechanics algorithm to achieve the best match between the probe model and the measurements. The result is a minimal cost state for probe 12, which describes the location and shape (i.e., an actual shape different from the free shape) of probe 12 and its deflection values (for a deflectable probe). A deflection value is a model parameter that describes a family of probe free shapes for a deflectable probe. Typically, a single deflection parameter affects several joints. Any joint rotation that differs from the rotation defined by the deflection parameter increases the cost function.

The probe mechanics algorithm uses a cost function, which is a weighted combination of intrinsic energy, position error and orientation error. Intrinsic energy represents the deviation of probe 12 from its free shape. Position error represents the error in position coordinates between the position transducer locations, given by the probe model and state, and the actual position measurements. Finally, orientation error represents the error in angular orientation coordinates between the position transducer orientations, given by the probe model and state, and the actual orientation measurements.

Figure 3:
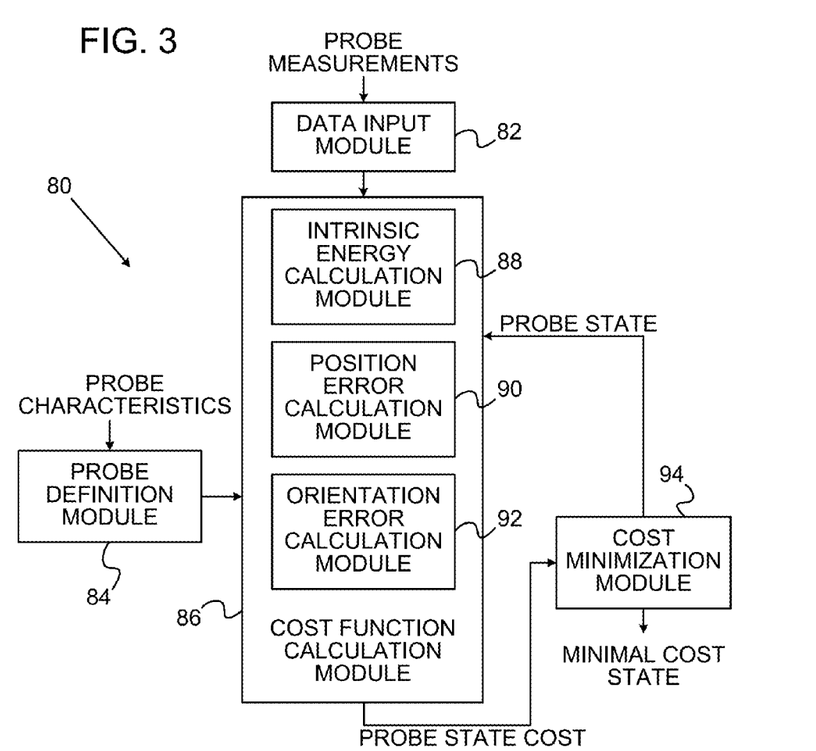
FIG. 3 a diagram that schematically shows details of a probe visualization system, in accordance with an embodiment of the present invention.

FIG. 3 is a block diagram 80 that schematically illustrates functional components of system 10 that are used in detection and compensation for artifacts experienced during position sensing of a probe, in accordance with an embodiment of the present invention. Specifically, this figure shows functional elements of software that runs on CPU 20 in the course of determining the position of probe 12. These functional elements are described in greater detail with referenced to the figures that follow.

Figure 4:
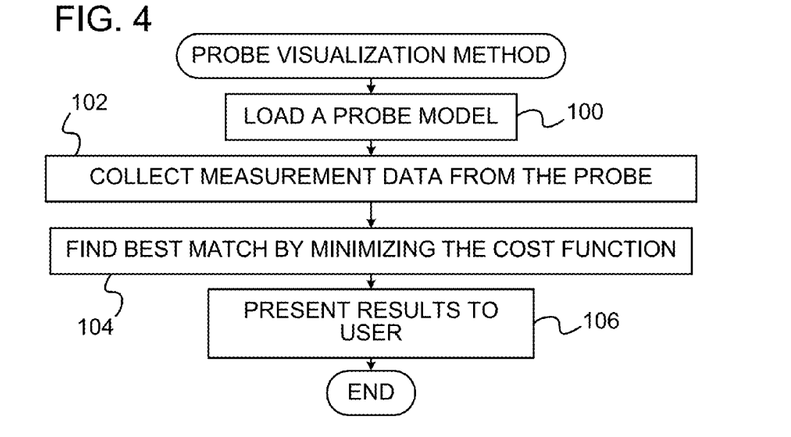
FIG. 4 is a flow diagram illustrating a probe visualization method, in accordance with an embodiment of the present invention.

FIG. 4 is a flow chart that schematically illustrates a method for visualizing probe 12 placed within subject 16, in accordance with an embodiment of the present invention. First, a probe model is pre-loaded into a probe definition module 84 (step 100). As discussed supra, the probe model describes the structure and the physical properties of probe 12 and is typically defined specifically for the type of catheter or other probe that is to be used. Medical professional 28 may select the model, for example, from a predefined list of options.

As medical professional 28 moves probe 12 in subject 16, a data input module 82 collects output position signals from electrodes 50, 52, 54 and 56 at regular intervals (step 102). For each position transducer 50, 52, 54, 56 defined in the probe model, data input module 82 receives a corresponding position measurement. The measurement can include a position vector (all types of transducers), direction (SAS) and/or full orientation (TAS). In addition, a measurement weight is associated with each measurement, depending on the confidence level of the measurement. The weight has a high value for precise measurements, and a low value for measurements with large expected error. Missing measurements will have weight of zero. The measurement parameters include:

$m_j$—Position measurement $m_j^{or}$—Orientation measurement (may include the full orientation or only direction)

$w_j^{msr}$—Weight of the measurement

After data input module 82 receives the inputs, a cost function calculation module 86 defines a probe state cost by applying a cost function to calculate the quality of the match between the probe model defined in probe definition module 84 and position data received from data input module 82 (step 104). This match defines the shape of the probe with the lowest cost according to the model, which in turn gives corrected coordinates of the points along the length of the probe that correspond to the locations of the position transducers. The probe state describes the location and shape of probe 12 and its deflection values (for a deflectable probe). CPU 20 determines the probe state at step 104. The state is given by the variables $\{x_0, r_k, d\}$:

$x_0$—The position of the first section starting point (i.e., in FIG. 2B.

$r_k$—The orientation of section k relative to section k−1 for $0 < k < N$ and the global orientation of the first section for k=0:

$$r_k \equiv \begin{cases} o_{k-1}^T \cdot o_k & 0 < k < N \\ o_0 & k = 0 \end{cases}$$

d—The values of the deflection parameters (for deflectable probes). These values do not affect the position and shape of probe 12, but they do affect the calculation of the cost function and thus affect the outcome of the probe mechanics algorithm.

As part of step 104, cost function calculation module 86 feeds the probe state cost to a cost minimization module 94, which applies a minimization algorithm to the cost function in order to find a minimal cost probe state that achieves a minimum value of the cost function (i.e., a best match). Finally, after determining the minimal cost probe state, display 38 presents map 40, showing the position of probe 12 in subject 16 (step 106). Typically, the probe position is shown in the form of an icon on the display, having a location, orientation and shape corresponding to model 60.

Figure 5:
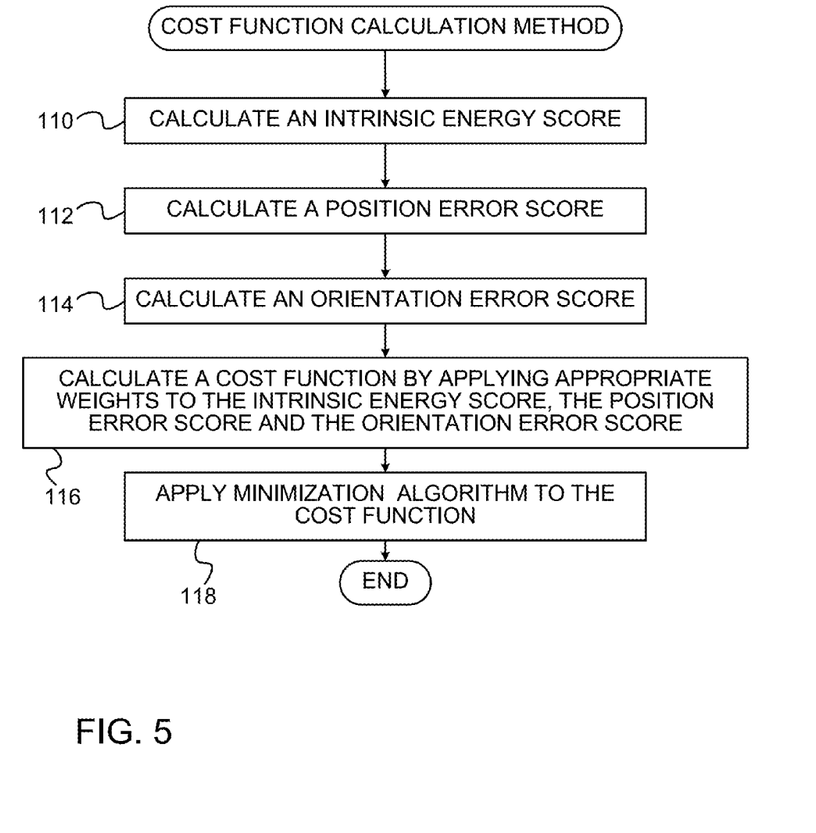
FIG. 5 is a flow diagram illustrating a cost function calculation method, in accordance with an embodiment of the present invention.

FIG. 5 is a flow chart that schematically illustrates a method by which cost function calculation module 86 applies a cost function to probe measurements received by data input module 82, in accordance with an embodiment of the present invention. The cost function depends on the probe model, the position measurements and the probe state. Minimizing the cost function with respect to the probe state $\{x_0, r_k, d\}$ achieves the best match between the probe model and the measurements. The calculation of the cost function also depends on a set of adaptive weights that are assigned to the measurements. The adaptive weights may dynamically change during the course of the cost function minimization and allow the algorithm to ignore measurements that totally disagree with the probe model (described hereinbelow). The adaptive weights are denoted by $w_j^{adaptive}$.

The cost function has three parts: intrinsic energy, position error and orientation error. First, an intrinsic energy calculation module 88 calculates an intrinsic energy score (step 110), which represents the deviation of probe 12 from its free shape (or a family of free shapes parameterized by deflection variables—for deflectable probes). For joints 68 and 70, the orientation difference between the actual relative orientation and the current deflection is calculated as:

$$dr_k = r_k^T \cdot G_k(d) \tag{1}$$

Intrinsic energy calculation module 88 converts this orientation difference to the bend and twist angles:

$$\{\alpha_k, \beta_k\} = \text{Angles}(dr_k) \tag{2}$$

The following is a definition of the function Angles (r) wherein r is a unitary 3×3 matrix that represents rotation:

$$\{\alpha, \beta\} \equiv \text{Angles}\left(\begin{bmatrix} r_{11} & r_{12} & r_{13} \\ r_{21} & r_{22} & r_{23} \\ r_{31} & r_{32} & r_{33} \end{bmatrix}\right)$$

$$\alpha = \arccos(r_{33})$$

$$\beta = \arctan(r_{11}(1 + r_{33}) - r_{31}r_{13}, r_{12}(1 + r_{33}) - r_{32}r_{13})$$

where:

arctan (x, y) is the angle between the vector (x, y) and the x axis. (3)

Returning to the cost function, intrinsic energy calculation module 88 calculates the intrinsic energy score using the probe model parameters $\{A_k, B_k\}$:

$$E^{int} = \sum_{k=1}^{N-1} A_k \alpha_k^2 + B_k \beta_k^2 \tag{4}$$

A position error calculation module 90 then calculates a position error score (step 112), which represents the position error between the locations of the position transducers given by the probe model and state, and the actual measurements. Position error calculation module 90 denotes the position of electrodes 50, 52, 54, 56 according to the probe model and state as $e_j$ and the corresponding measurements as $m_j$. Position error calculation module 90 calculates the weighted position error as follows:

$$E^{pos} = \sum_{j=0}^{M-1} w_j^{model} w_j^{msr} w_j^{adaptive} (e_j - m_j)^2 \tag{5}$$

where M is the number of position transducers.

An orientation error calculation module 92 then calculates an orientation error score (step 114), which represents the orientation error between the position of electrodes 50, 52, 54, 56, given by the probe model and state, and the actual measurements m received by data input module 82. The orientation of the various points along probe 12, represented by the probe model, is a discontinuous function, which has abrupt changes at model joints (unlike the position). After calculating the orientations of all the relevant position transducers $e_j^{or}$ according to the model, orientation error calculation module 92 calculates the angular difference with respect to the measured orientation $m_j^{or}$:

$$\{a_j, b_j\} = \text{Angles}((e_j^{or})^T \cdot m_j^{or}) \tag{6}$$

and the total orientation error:

$$E^{or} = \sum_{j=0}^{M-1} w_j^{model} w_j^{msr} w_j^{adaptive} (a_j^2 + b_j^2) \tag{7}$$

Cost function calculation module 86 then calculates a cost function as a weighted combination of the three parts (i.e., intrinsic energy, position error and orientation error) (step 116):

$$\text{Cost}(x_0, r_k, d) = \lambda^{int} E^{int} + \lambda^{pos} E^{pos} + \lambda^{or} E^{or} \tag{8}$$

The values $\{\lambda^{int}, \lambda^{pos}, \lambda^{or}\}$ describe the relative importance of deviation of probe 12 from its free shape vs. the position and orientation errors.

As discussed supra, cost function calculation module 86 feeds the calculated cost function (i.e., the probe state cost) to minimization module 94, which minimizes the function Cost $(x_0, r_k, d)$ with respect to the probe state variables in order to achieve the best match between the probe model and the actual measurements received by data input module 82 (step 118). The minimization can be done by any suitable numerical method. In one embodiment of the present invention, for example, cost function calculation module 86 uses the Broyden—Fletcher—Goldfarb—Shanno (BFGS) minimization algorithm.

Since minimizing the cost function in step 118 employs an iterative algorithm (i.e., each iteration of the algorithm improves the estimate of the solution), and the position and shape of probe 12 change slowly between measurements, the inventors have found that it is usually sufficient to apply only one iteration of the cost function minimization algorithm for each successive measurement. After each minimization iteration, cost minimization module 94 feeds a probe state to cost function calculation module 86, which may change the adaptive weights of the measurements according to the individual transducer position errors. Typically, the weights corresponding to impedance-sensing electrodes are adapted, while more accurate sensors, such as magnetic position sensors, retain a weight of 1.

Cost function calculation module 86 performs the weight adaptation procedure as follows:

1. Compute Initial New Weights $$w_j^{new} = \max\left(\exp\left(\frac{(e_j - m_j)^2}{2\sigma_j^2}\right), 0.0001\right) \tag{9}$$

wherein the value σ is larger for sensors with a large expected error, thereby allowing a greater error prior to a decrease in a corresponding adaptive weight.

2. Normalize the Initial Weights $$w_j^{new} \leftarrow \frac{w_j^{new}}{\text{mean}(w_j^{new})} \quad (10)$$

3. Limit each Weight from above by 1

$$w_j^{new} \leftarrow \min(w_j^{new}, 1) \quad (11)$$

4. Update the Adaptive Weights $$w_j^{adaptive} \leftarrow 0.9 w_j^{adaptive} + 0.1 w_j^{new} \quad (12)$$

This adaptation procedure allows the minimization process to ignore position transducers that consistently give large errors, yet does not allow it to ignore too many position transducers.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but is not intended to be exhaustive or limiting to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated. It is intended that the appended claims cover all such features and advantages of the invention that fall within the spirit and scope of the present invention. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention.

What is claimed is:

1. A method for visualization, comprising:
receiving an input indicative of respective apparent coordinates of a plurality of points disposed along a length of a probe inside a body of a subject, wherein the probe comprises a plurality of position transducers along the length of the probe inside a body of a subject;
applying a model of known mechanical properties of the probe to the apparent coordinates so as to compute a cost function with respect to shapes that can be assumed by the probe in the body;
choosing a shape responsively to the cost function;
generating corrected coordinates of the points along the length of the probe based on the shape; and
displaying a representation of the probe using the corrected coordinates, wherein the cost function is computed by: calculating an intrinsic energy representing a deviation of the probe from a free shape of the probe; calculating a position error between the model of known mechanical properties of the probe and the input indicative of respective apparent coordinates of the plurality of points disposed along the length of the probe; calculating an orientation error between the model of known mechanical properties of the probe and the input indicative of respective apparent coordinates of the plurality of points disposed along the length of the probe; and calculating the cost function as a weighted average of the intrinsic energy, the position error and the orientation error.

2. The method according to claim 1, wherein the probe comprises a catheter, and wherein receiving the input comprises receiving a measurement of the apparent coordinates of the catheter within a heart of the subject.

3. The method according to claim 1, wherein the input is selected from a group consisting of a position vector, a direction measurement and a full orientation measurement.

4. The method according to claim 1, wherein receiving the input comprises receiving inputs from position transducers disposed along the length of the probe, and wherein each of the plurality of points corresponds to a respective location of a position transducer.

5. The method according to claim 4, wherein the position transducer is selected from a group consisting of an impedance measurement electrode, a single-axis magnetic sensor and a three-axis magnetic sensor.

6. The method according to claim 1, wherein the model of known mechanical properties of the probe comprises:
multiple sections of the probe;
a length of each of the sections;
a rotation matrix defining relative rotation of each of the sections with regard to a preceding section; and
a location on the probe of each of the plurality of points.

7. The method according to claim 6, wherein the rotation matrix comprises a function of one or more deflection parameters of the probe.

8. A computer program product for controlling a peripheral device, the computer program product comprising:
a computer readable medium being of a non-transitory nature and having computer usable code embodied therewith, the computer usable program code comprising:
computer usable code configured for receiving an input indicative of respective apparent coordinates of a plurality of points disposed along a length of a probe inside a body of a subject, wherein the probe comprises a plurality of position transducers along the length of the probe inside a body of a subject;
computer usable code configured for applying a model of known mechanical properties of the probe to the apparent coordinates so as to compute a cost function with respect to shapes that can be assumed by the probe in the body;
computer usable code configured for choosing a shape responsively to the cost function;
computer usable code configured for generating corrected coordinates of the points along the length of the probe based on the shape; and
computer usable code configured for displaying a representation of the probe using the corrected coordinates, wherein the cost function is computed by: calculating an intrinsic energy representing a deviation of the probe from a free shape of the probe; calculating a position error between the model of known mechanical properties of the probe and an input indicative of respective apparent coordinates of the plurality of points disposed along the length of the probe; calculating an orientation error between the model of known mechanical properties of the probe and the input indicative of respective apparent coordinates of the plurality of points disposed along the length of the probe; and calculating the cost function as a weighted average of the intrinsic energy, the position error and the orientation error.

9. The computer program product according to claim 8, wherein the probe comprises a catheter, and wherein receiving the input comprises receiving a measurement of the apparent coordinates of the catheter within a heart of the subject.

10. The computer program product according to claim 8, wherein the input is selected from a group consisting of a position vector, a direction measurement and a full orientation measurement.

11. The computer program product according to claim 8, wherein receiving the input comprises receiving inputs from position transducers disposed along the length of the probe, and wherein each of the plurality of points corresponds to a respective location of a position transducer.

12. The computer program product according to claim 11, wherein the position transducer is selected from a group consisting of an impedance measurement electrode, a single-axis magnetic sensor and a three-axis magnetic sensor.

13. The computer program product according to claim 8, wherein the model of known mechanical properties of the probe comprises:
multiple sections of the probe;
a length of each of the sections;
a rotation matrix defining relative rotation of each of the sections with regard to a preceding section; and
a location on the probe of each of the plurality of points.

14. The computer program product according to claim 13, wherein the rotation matrix comprises a function of one or more deflection parameters of the probe.

15. A probe visualization apparatus, comprising:
an interface, which is configured to receive an input indicative of respective apparent coordinates of a plurality of points disposed along a length of a probe, wherein the probe comprises a plurality of position transducers along the length of the probe inside a body of a subject; and
a processor, which is configured to
receive the input from the interface;
apply a model of known mechanical properties of the probe to the apparent coordinates so as to compute a cost function with respect to shapes that can be assumed by the probe in the body;
choose a shape responsively to the cost function; and
generate corrected coordinates of the plurality of position transducers along the length of the probe based on the shape, wherein the cost function is computed by the processor by: calculating an intrinsic energy representing a deviation of the probe from a free shape of the probe; calculating a position error between the model of known mechanical properties of the probe and an input indicative of respective apparent coordinates of the plurality of points disposed along the length of the probe; calculating an orientation error between the model of known mechanical properties of the probe and the input indicative of respective apparent coordinates of the plurality of points disposed along the length of the probe; and calculating the cost function as a weighted average of the intrinsic energy, the position error and the orientation error.

16. The apparatus according to claim 15, and comprising a display, wherein the processor presents a representation of the probe on the display using the corrected coordinates.

17. The apparatus according to claim 15, wherein the probe comprises a catheter, and wherein the input comprises a measurement of the apparent coordinates of the catheter within a heart of the subject.

18. The apparatus according to claim 15, wherein the input is selected from a group consisting of a position vector, a direction measurement and a full orientation measurement.

19. The apparatus according to claim 15, wherein the probe comprises position transducers disposed along the length of the probe, and wherein each of the plurality of points corresponds to a respective location of a position transducer.

20. The apparatus according to claim 19, wherein the position transducer is selected from a group consisting of an impedance measurement electrode, a single-axis magnetic sensor and a three-axis magnetic sensor.

21. The apparatus according to claim 15, wherein the model of known mechanical properties of the probe comprises:
multiple sections of the probe;
a length of each of the sections;
a rotation matrix defining relative rotation of each of the sections with regard to a preceding section; and
a location on the probe of each of the plurality of points.

22. The apparatus according to claim 21, wherein the rotation matrix comprises a function of one or more deflection parameters of the probe.

* * * * *